US012685567B2

(12) United States Patent
Smith et al.

(10) Patent No.: US 12,685,567 B2
(45) Date of Patent: Jul. 21, 2026

(54) VISUALISATION DEVICE TO PROVIDE INFORMATION ON THE DESIRED SHAPE OF A POSTERIOR SPINAL ROD

(71) Applicants: Justin Smith, Charlottesville, VA (US); K-SPINE GMBH, Kufstein (AT); IGNITE-CONCEPTS GMBH, Attiswil (CH)

(72) Inventors: Justin Smith, Charlottesville, VA (US); Heiko Koller, Kufstein (AT); Tom Overes, Attiswil (CH)

(73) Assignees: K-SPINE GMBH, Kufstein (AT); IGNITE-CONCEPTS GMBH, Attiswill (CH)

( * ) Notice: Subject to any disclaimer, the term of this patent is extended or adjusted under 35 U.S.C. 154(b) by 137 days.

(21) Appl. No.: 18/683,243

(22) PCT Filed: Aug. 19, 2022

(86) PCT No.: PCT/EP2022/073247
§ 371 (c)(1),
(2) Date: Feb. 12, 2024

(87) PCT Pub. No.: WO2023/021204
PCT Pub. Date: Feb. 23, 2023

(65) Prior Publication Data
US 2025/0134555 A1     May 1, 2025

(30) Foreign Application Priority Data
Aug. 19, 2021    (CH) ................................ CH70181/21

(51) Int. Cl.
*A61B 50/30*        (2016.01)
*A61B 17/70*        (2006.01)
(Continued)

(52) U.S. Cl.
CPC ...... *A61B 17/7013* (2013.01); *A61B 17/8863* (2013.01); *A61B 34/25* (2016.02);
(Continued)

(58) Field of Classification Search
CPC .......... A61B 17/06114; A61B 17/7013; A61B 17/8863; A61B 34/10; A61B 50/30;
(Continued)

(56) References Cited

U.S. PATENT DOCUMENTS 8,226,669 B2 *    7/2012    Detruit .................. A61F 2/0095
                                                    623/23.72
2005/0033430 A1 *    2/2005    Powers .............. A61B 17/7059
                                                    606/76
(Continued)

FOREIGN PATENT DOCUMENTS

CN          201659766 U     12/2010
CN          211710436 U     10/2020
WO          2018203100 A1     11/2018

OTHER PUBLICATIONS

International search report and written opinion of the International Searching Authority issued in connection with PCT/EP2022/073247.

(Continued)

*Primary Examiner* — Luan K Bui
(74) *Attorney, Agent, or Firm* — Gallium Law; Jacob Panangat

(57)        ABSTRACT
A rod shape visualisation device (1) is proposed for providing information on the desired shape of a posterior spinal rod during a bending process whilst being arranged in a sterile operation area. The rod shape visualisation device (1) comprises: (a) a sterile case (10) comprising a housing portion (11) including an entrance aperture (12) and a cover (13), sized and shaped to seal the entrance aperture (12), the
(Continued)

sterile case (10) further comprising an inner lumen (14) configured to come in contact with non-sterile or sterile objects, and (b) a non-sterile or sterile visualisation template (40) comprising a displaying side providing information on the desired shape of a posterior rod. The rod shape visualisation device (1) defines a first, open state in which the cover (13) is open, and a second, closed state in which the cover (13) is closed, wherein in the closed state, the displaying side of the visualisation template (40) is visibly arranged in the inner lumen (14).

26 Claims, 12 Drawing Sheets

(51) Int. Cl.

| | | |
|---|---|---|
| *A61B 17/88* | (2006.01) | |
| *A61B 34/00* | (2016.01) | |
| *A61B 50/31* | (2016.01) | |
| *A61B 34/10* | (2016.01) | |
| *A61B 50/00* | (2016.01) | |
| *A61B 90/00* | (2016.01) | |

(52) U.S. Cl.
CPC ........ *A61B 50/31* (2016.02); *A61B 2034/102* (2016.02); *A61B 2050/0053* (2016.02); *A61B 2050/311* (2016.02); *A61B 2090/0808* (2016.02)

(58) Field of Classification Search
CPC .................... A61B 50/31; A61B 50/33; A61B 2017/00955; A61B 2017/568; A61B 2034/108; A61B 2050/005; A61B 2050/3006; A61B 2050/3015; A61B 2090/0813; A61B 2090/376
USPC ................................................. 206/363, 438
See application file for complete search history.

(56) References Cited

U.S. PATENT DOCUMENTS

| | | | |
|---|---|---|---|
| 2013/0327667 A1* | 12/2013 | Grabowski | ........... A61F 2/0095 |
| | | | 53/467 |
| 2014/0346072 A1* | 11/2014 | Jacobson | ............... A61B 50/33 |
| | | | 53/449 |
| 2015/0122681 A1* | 5/2015 | Dacey | .................... A61B 50/00 |
| | | | 206/363 |
| 2017/0135706 A1 | 5/2017 | Frey et al. | |
| 2020/0197149 A1* | 6/2020 | Folger | ................... A61F 2/0095 |
| 2020/0375636 A1* | 12/2020 | Hobeika | ............ A61B 17/7074 |
| 2021/0000511 A1* | 1/2021 | Park | ...................... G06T 7/0012 |

OTHER PUBLICATIONS

Swiss search report issued in connection with CH70181/21.

* cited by examiner

1

32/43/62

1

32/43/62

70 / 71

1

1

VISUALISATION DEVICE TO PROVIDE INFORMATION ON THE DESIRED SHAPE OF A POSTERIOR SPINAL ROD

TECHNICAL FIELD OF THE INVENTION

The present invention relates to a rod shape visualisation device. The proposed rod shape visualisation device allows a surgeon to accurately verify the size and shape of an intra-operatively manually bent spinal rod in relation to the pre-operatively planned size and shape of the spinal rod. The rod shape visualisation device includes a sterile case for use within the sterile operation area, in which a non-sterile template with information on the planned shape can be placed. The non-sterile template may be a combination of a paper print or electronic device arranged in a pouch or shell which stabilizes the paper print or electronic device.

BACKGROUND OF THE INVENTION

In orthopaedic surgery around the spine, posterior spinal stabilisation systems are often placed to a target site to realign, correct and/or stabilise the spinal column to compensate for malalignment caused by for example degeneration of the spine, born malalignments, such as excessive lordosis, kyphosis and scoliosis, and for example trauma, such as fractures. A typical posterior spinal stabilisation system consists of multiple pedicle screws that are connected by a rod. In a first step, at different levels of the spinal column, the pedicle screws are inserted through the pedicle bone into vertebral bodies. In a second step, the pedicle screws are connected by a rod, having a desired shape or curvature. Using a spinal column persuading instrument, the vertebral bodies including the pedicle screws are forced towards the rod (or vice versa). When the rod has reached the end position within a rod receiving head of the pedicle screw, the rod is rigidly fixated to the rod receiving head by tightening a set screw against the rod.

Most commonly, these rods are manually contoured using a rod bender during surgery. One typical device, the so-called French rod bender, comprises a three-point bending system in association with two longer lever-shaped handles or arms. Each handle comprises a post which is arranged at a small distance from the pivot point, wherein the pivot point itself forms the third post. A rod is placed between these three posts and by rotating the handles, the first and second posts rotate around the third post, as the rod is being bent.

The shape of the rod is typically based upon a pre-operative planning procedure. Based on X-rays, computed tomography (CT) scans, magnetic resonance imaging (MRI) scans, or similar of the patient, the operating surgeon plans the desired shape of the rod. The shape then is reproduced during surgery and the rod is implanted. During surgery, X-ray images outside the sterile area provide feedback on the desired shape. A set of numerical values that describes the rod shape can provide the same information. The operating surgeon usually has to bend the rod in multiple steps and/or bend the rod when already being engaged in situ in the pedicle screws. The correction is verified against the pre-operative planning by taking intra-operative X-ray images.

Although sophisticated planning software for pre-operative surgical planning provides the ability to exactly define the desired rod shape, it is difficult for the surgeon to verify this desired rod shape whilst being within the sterile operating area. Obtaining manually an intended rod shape and rod angle can be cumbersome and imprecise. It remains uncertain if the desired shape that has been reproduced during the manual rod-bending process matches the desired size and shape information which is present in the non-sterile area. In addition, multiple rod bendings and changes of rod alignment of a single rod shall be avoided to lower the risk of fatigue failure of the rod at the bending zones.

The sterile operation area typically is the area around or adjacent to the patient in which the surgeon is performing the surgery. Therefore, the non-sterile area is the area outside the said sterile operation area. Objects may be handed from the non-sterile area into the sterile operation area, but it has to be always ensured that either unsterile objects will be encapsulated in a sterile barrier or case, or the objects are sterile.

Due to imperfect contoured rod shape, the desired spinal realignment result may not always be as planned, and high forces are required to be able to fixate the rod in the pedicle screw. As a result, for example proximal junction kyphosis (PJK) and proximal junctional failure (PJF) and screw pull out are the major complications and challenges with adult multilevel spinal fusion surgeries. In addition, under-contouring of rods, for example introduction of insufficient lumbar lordosis (curvature) may result in "flatback syndrome" with significant impact on the patient's ability to stand upright and ambulate. Over-contouring of rods, for example introduction of excessive lumbar lordosis (curvature) significantly increases the risk of PJK and PJF. Often the complications lead to the need of revision surgery.

Thus, in view of the above, there is a need for a device that visualises the intended curvature of a spinal rod based on pre-operative planning. Moreover, this device shall be used in the sterile operation area and is to provide the surgeon with accurate feedback on the size and/or shape of the spinal rod. Furthermore, the visualisation device must not impose any risk of contamination of the sterile operation area or the tools that are used in this area. Moreover, by using dedicated software it shall be possible to scale a pre-operative planning image to real size for printing it in an accurately-sized manner on a selected paper format.

SUMMARY OF THE INVENTION

It is an object of the present invention to overcome at least some of the problems associated with the contouring or shaping of posterior spinal rods, which are elements of a posterior spinal stabilisation construct. There is a need for a device that visualises the desired size and shape of a spinal rod that can be used intra-operatively and can further be used within the sterile operation area. The rod shape visualisation device must depict or provide information on the desired shape of a posterior rod, and it allows the surgeon to hold the physical rod adjacent to this information and so verify the bending result.

According to a first aspect of the invention, there is provided a rod shape visualisation device or kit comprising a sterile case and a visualisation template as recited in claim 1.

The sterile case is intended to receive and hold the visualisation template when being arranged in the sterile operation area. Therefore, the sterile case is sized and shaped to comprise an open state and a closed state, wherein in the open state either a non-sterile or sterile visualisation template can be transferred out of the non-sterile area into the sterile area, and the template be placed into the sterile case. Upon closing the case, the sterile case forms a barrier and separates its content from the sterile operation area. In one embodiment, the case top or cover is transparent to allow the visualisation template to be visually inspected through the case cover.

According to a second aspect of the invention, there is provided a visualisation template including information of the desired rod shape, which is created by means of a pre-operative planning, e.g. using a planning software solution, and it is printed on a medium such as a paper, cardboard, foil, plastic or equivalent media or shown using a tablet, personal computer (PC), smartphone or other digital electronic illustration device. The visualisation template is a patient-specific template and therefore typically only used once.

According to a third aspect of the invention, there is provided a template holder, such as a shell, or an inner box with an inner box cover, which holds a flexible non-sterile template, such as a paper print and so stabilizes the flexible sheet for safe placement from the non-sterile area into the sterile operation area.

According to a fourth aspect of the invention, there is provided a visualisation template, which is projected or displayed by a screen of an electronic device, such as a tablet computer.

According to a fifth aspect, there is provided a rod shape visualisation kit, comprising the rod shape visualisation device and scaling software.

According to a sixth aspect, there is provided a method of visualisation of a spinal rod size and shape in a sterile surgical area.

Other aspects of the invention are recited in the dependent claims attached hereto.

BRIEF DESCRIPTION OF THE DRAWINGS

Other features and advantages of the invention will become apparent from the following description of non-limiting example embodiments, with reference to the appended drawings, in which.

DETAILED DESCRIPTION OF THE INVENTION

Figures 1A, 1B:
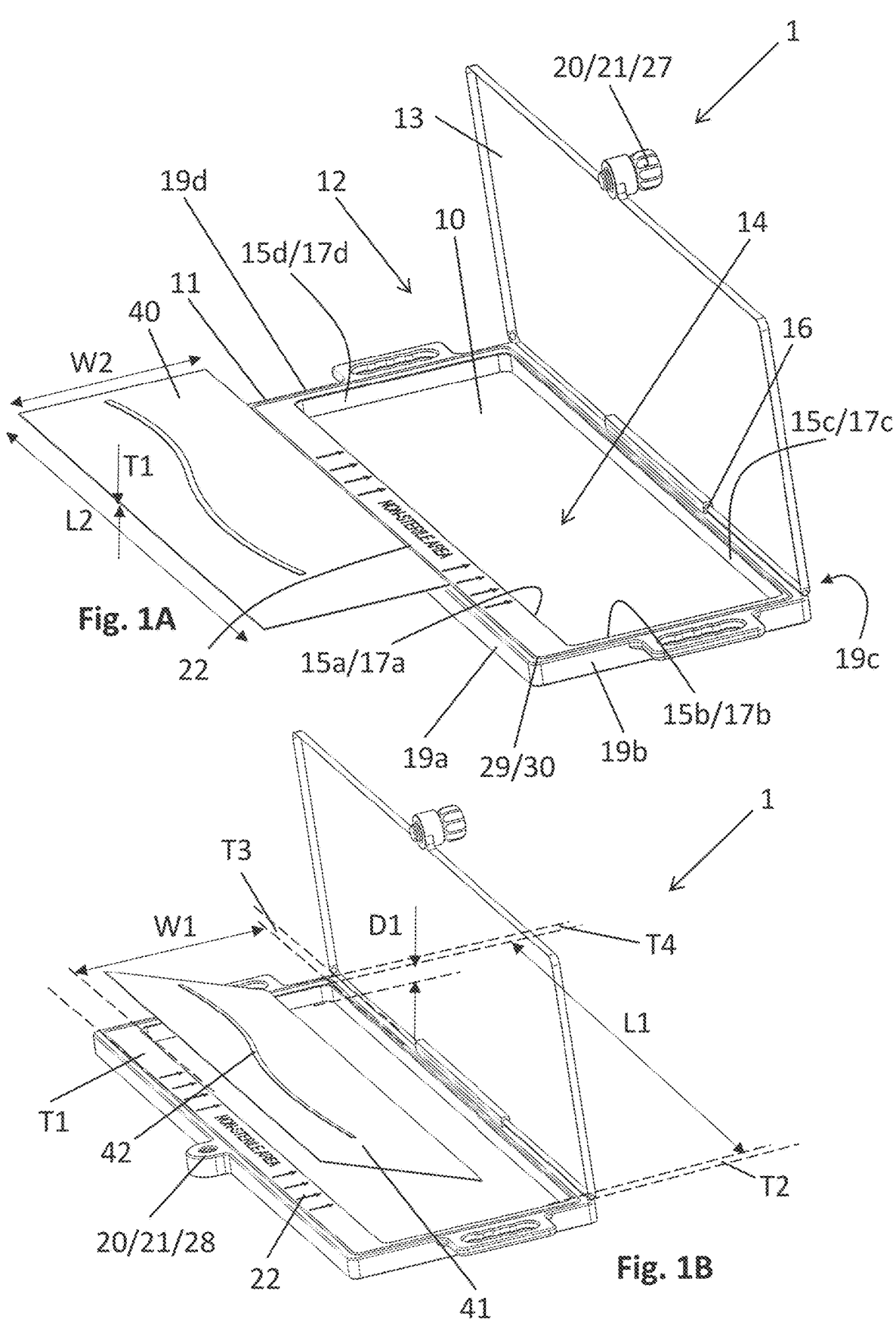
FIGS. 1A to 1D depict an example rod shape visualisation device in an open state, according to a first embodiment of the present invention.

The embodiments of the present invention will now be described in detail with reference to the attached figures. The embodiments are described in the context of a posterior rod (which is a component of a posterior spinal stabilisation construct) which is to be manually contoured to a desired size and shape, and a rod shape visualisation device comprising a sterile case and a visualisation template which provide the operating surgeon with exact information on the said desired size and shape. Although the invention is specifically described in this context, the teachings of the invention are not limited to this environment. The teachings of the present invention are equally applicable to shape visualisation devices to be used in connection with other bones, bone plates, nails, external, and internal bone fixators, for instance. When the words first and second are used to refer to different elements, it is to be understood that this does not necessarily imply or mean that the first and second elements are somehow structurally substantially different elements or that their dimensions are substantially different unless implicitly or explicitly stated.

A rod shape visualisation device in this context means a displaying apparatus or unit, which provides information to the operating surgeon on the rod shape and is formed as an outer case, box, container, envelope, pouch, and it holds an exchangeable visualisation template.

A sterile case in this context means a box, container, envelope, bag, pouch, or similar that is sized and shaped to hold a specific object or specific objects which may be non-sterile. The sterile case has, defines or features an open state and a closed state, where in the said closed state, the case forms a barrier inhibiting the non-sterile object from contaminating the environment around the sterile case, and where in the said open state, access is provided to the interior of the sterile case. The sterile case may be a reusable or single-use object. In one example, the sterile case is configured to be reprocessed by common hospital reprocessing procedures, such as by washing and/or steam-sterilisation.

A visualisation template in this context means an object displaying or showing information on the desired shape of the rod. The information may be visualised as a realistic or abstract image of the desired rod contour, a graphical image or representation, but it May also be a set of numbers, coordinates, etc. which provide information on the size and shape. A visualisation template may be made of a medium or material such as a sheet of paper, cardboard, foil, plastic, aluminium, steel, or equivalent media, or combinations thereof. Alternatively, a visualisation template can be a screen of an electronic device, such as a tablet computer with for example a touchscreen, which is projecting or displaying the desired size and shape. In one embodiment, the visualisation device may communicate via wireless or wired communication means, e.g. by means of wireless local area network (WLAN) or Bluetooth technologies for real time updates to the template alignment goal within the sterile case. Messages may be received for example from an imaging device, such as a radiographic imaging device, navigational device, robotic device, and/or another surgical planning device.

Figures 1C, 1D:
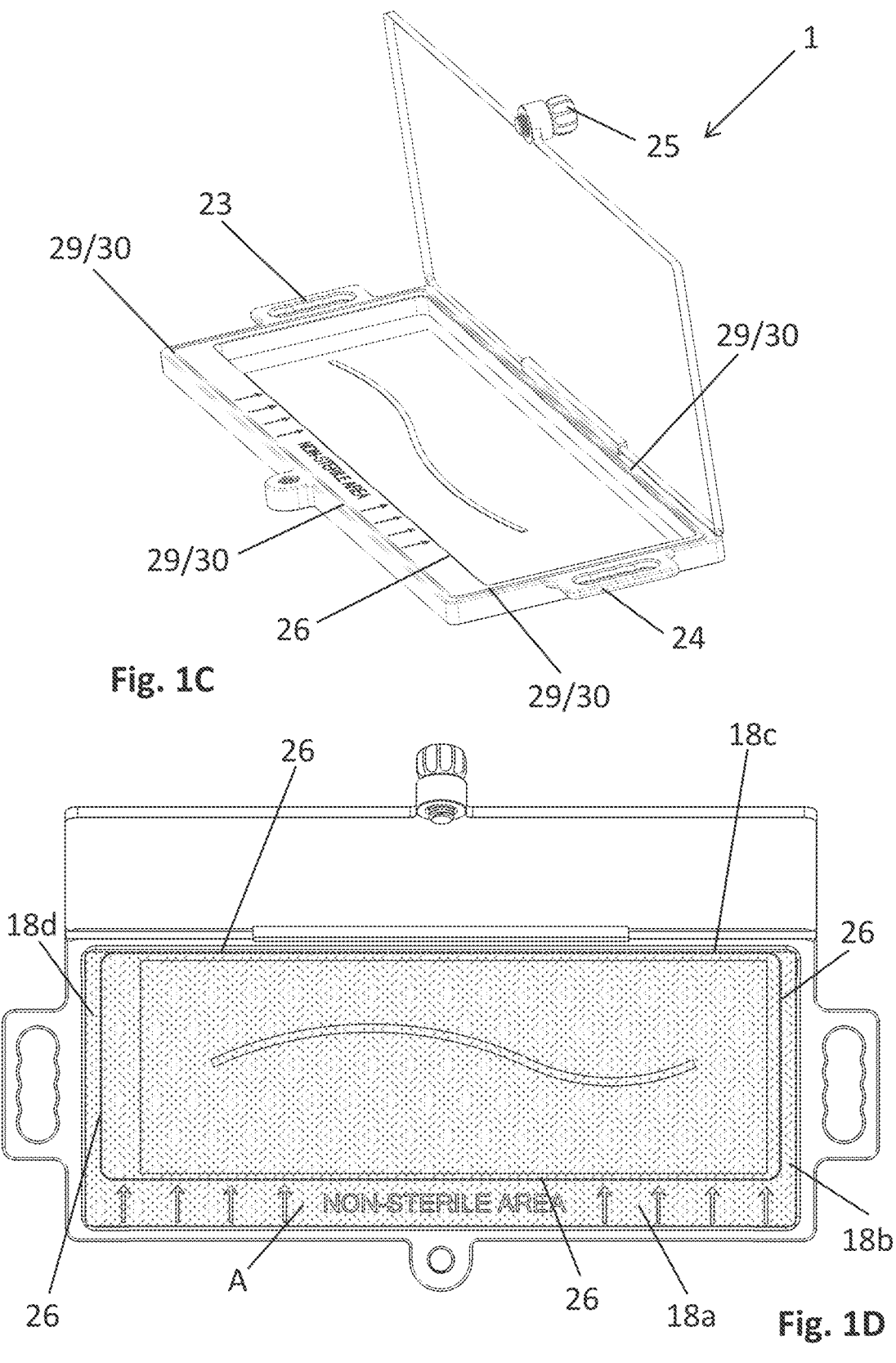
Figures 1E, 1F, 1G:
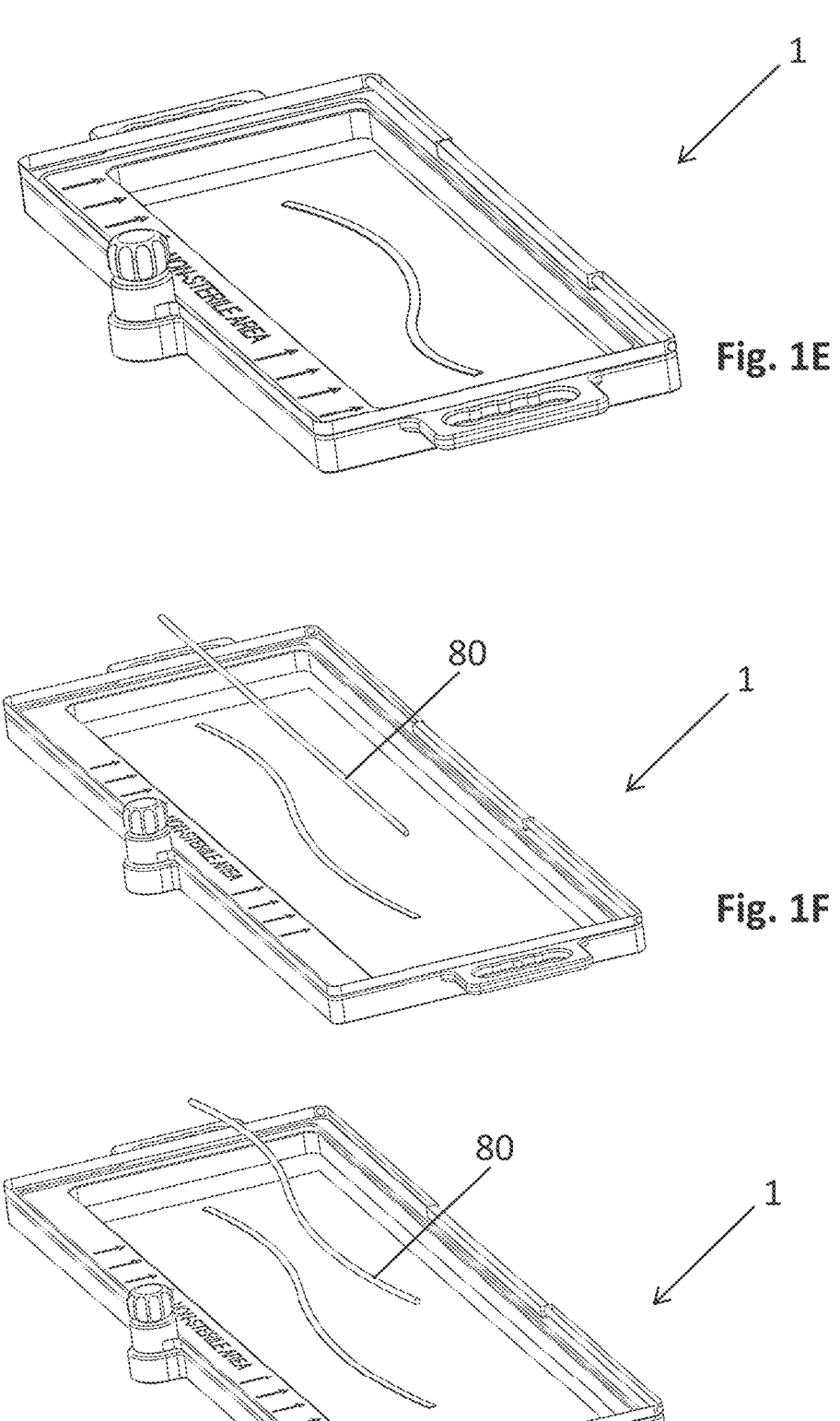
FIGS. 1E to 1G depict the rod shape visualisation device of FIGS. 1A to 1D in a closed state, according to the first embodiment of the present invention.

FIGS. 1A to 1G show an example rod shape visualisation device 1 in different perspective views. FIGS. 1A to 1D show the device in a first, open status, state or configuration, while FIGS. 1E to 1G show the device in a second, closed status, state or configuration.

The example rod shape visualisation device 1 comprises a sterile case 10 serving as a sterility barrier, and a visualisation template 40 serving as an information providing means or element. The sterile case 10 comprises a housing (portion) or main body portion 11 with an entrance aperture or opening 12 and a closure lid or cover 13, which is sized and shaped to close the entrance aperture 12. In this example, the housing portion is a box-shaped housing portion having an inner lumen, cavity, or space 14. The boxed-shaped housing portion 11 has a bottom wall and side walls, namely a first sidewall 15a, a second sidewall 15b, a third sidewall 15c, and a fourth sidewall 15d. Each sidewall respectively has an inside surface or wall 17a, 17b, 17c, 17d, a topside 18a, 18b, 18c, 18d, and an outside surface or wall 19a, 19b, 19c, 19d. The first, second, third, and fourth topsides, respectively, have a first, second, third, and fourth thickness 'T1', 'T2', 'T3', 'T4'. The inner lumen has an average first depth 'D1', an average first width 'W1' and an average first length 'L1'. In one example, the inner lumen 14 has a first length of at least 60 cm, more preferably at least 70 cm.

In this example, the cover 13 is connected to the housing at one sidewall by a hinge coupling or mechanism 16. The hinge coupling allows the cover to be rotated into an open position or a closed position, and so it defines the open and closed states of the rod shape visualisation device 1. The hinge coupling is configured as a pin in a knuckle hinge, but it may instead be formed as a compliant flexure mechanism, a taped foil, a nose in a recess coupling, or any form-fit mechanism that allows rotation of the cover in relation to the box-shaped housing portion. It is to be noted that a hinged connection between the housing portion 11 and the cover 13 is not a mandatory feature. A cover can also be placed loosely on top of the housing to close the inner lumen 14.

To rigidly close the cover 13, and to provide the required sealing characteristics, the sterile box in this example comprises at least one releasable locking mechanism 20. This locking mechanism can be configured in many alternative designs. For example, as depicted, the releasable locking mechanism 20 is configured as a threaded mechanism 21 having a threaded bolt 27 which engages into a complementarily shaped threaded bore or hole 28. Alternatively, other closing mechanisms, such as an automatically engaging and releasable klick finger, a friction-based ball bearing, a magnetic mating of the cover and the housing portion (a magnetic locking mechanism), an adhesive tape, etc., may achieve the same result.

Advantageously, the cover 13 may be made of a transparent material providing visibility of the visualisation template 40 through the cover.

As described, the sterile case 10 is configured to hold a non-sterile object, such as the visualisation template 40. In a typical use scenario, the sterile case is placed in the sterile operation area on a sterile table or similar. A first, sterile assistant or surgeon will open the sterile case, allowing the non-sterile visualisation template 40 to be placed in there by a second, non-sterile assistant. After placement, the sterile assistant or surgeon will close and optionally seal the sterile case.

During this process, any area which either comes in contact with the non-sterile assistant or the non-sterile visualisation template 40, must be considered contaminated.

Hence, only certain areas of the sterile case 10, which can safely be sealed off may come in contact with non-sterile objects or persons.

As shown in FIGS. 1A to 1G, in this example the housing portion, and in particular at least one of the topsides 18a, 18b, 18c, 18d of the sidewalls or the periphery 26 of the inner lumen 14 comprises at least one marking 22 which indicates the border 30 of the area 'A' in which contact with non-sterile objects or persons is allowed. In one example, the non-sterile area 'A' is of a different colour. At least one side of the housing portion 11 and/or the cover 13 may be electrically conductive to allow it to operate as a touchscreen.

In this example, the housing portion 11 comprises a sealing rim or ring 29, which is arranged between the topsides 18a, 18b, 18c, 18d and the cover. The sealing ring 29 may be made of a flexible or rubber-like material, which deforms upon compression. By pressing the cover down using the closing mechanism, the non-sterile area is sealed from the surrounding sterile operation area. In one embodiment, the sealing rim 29 defines the border of area 'A'.

Furthermore, the housing portion 11 and/or the cover 13 may comprise a first, second or third handle 23, 24 facilitating the use of the rod shape visualisation device 1. The first and second handles 23, 24 can be used to carry the rod shape visualisation device 1, or to stabilise the device while opening the cover. The third handle can be used to open and close the cover 13.

The visualisation template as shown in the figures is a thin medium or element having a first average height H1, an average second width W2, and an average second length L2. The displaying side 41 or information-showing side of the visualisation template 40 comprises a graphical image or representation 42 of the desired contour, shape, and/or size of the posterior rod.

FIGS. 1A to 1G further show the method when operating the rod shape visualisation device 1.

FIGS. 1A and 1B show the visualisation template being placed into the sterile case.

FIGS. 1C and 1D show the visualisation template being in situ in the sterile case.

FIG. 1E shows the sterile case in the closed state. In the closed state, the displaying side 41 of the visualisation template 40 is arranged in the inner lumen 14 so that it is visible to the outside of the sterile case.

FIG. 1F shows a straight, unbent rod 80, which is held adjacent to the visualisation template.

FIG. 1G shows how the rod 80 has been contoured and sized according to the desired size and shape as depicted on the visualisation template.

Figures 2A, 2B:
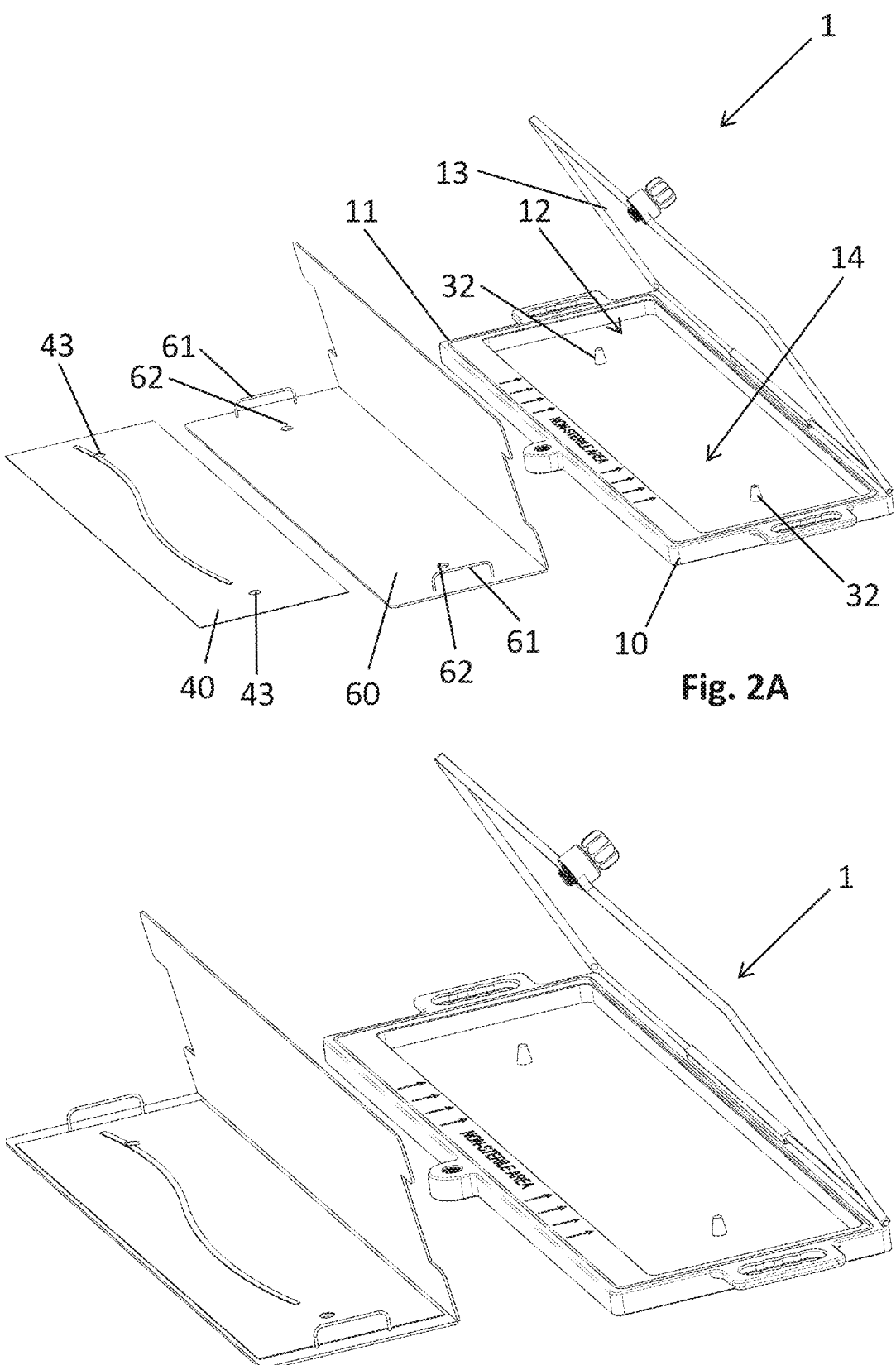
FIGS. 2A to 2D depict an example rod shape visualisation device in an open state, according to one further embodiment of the present invention.
Figures 2C, 2D:
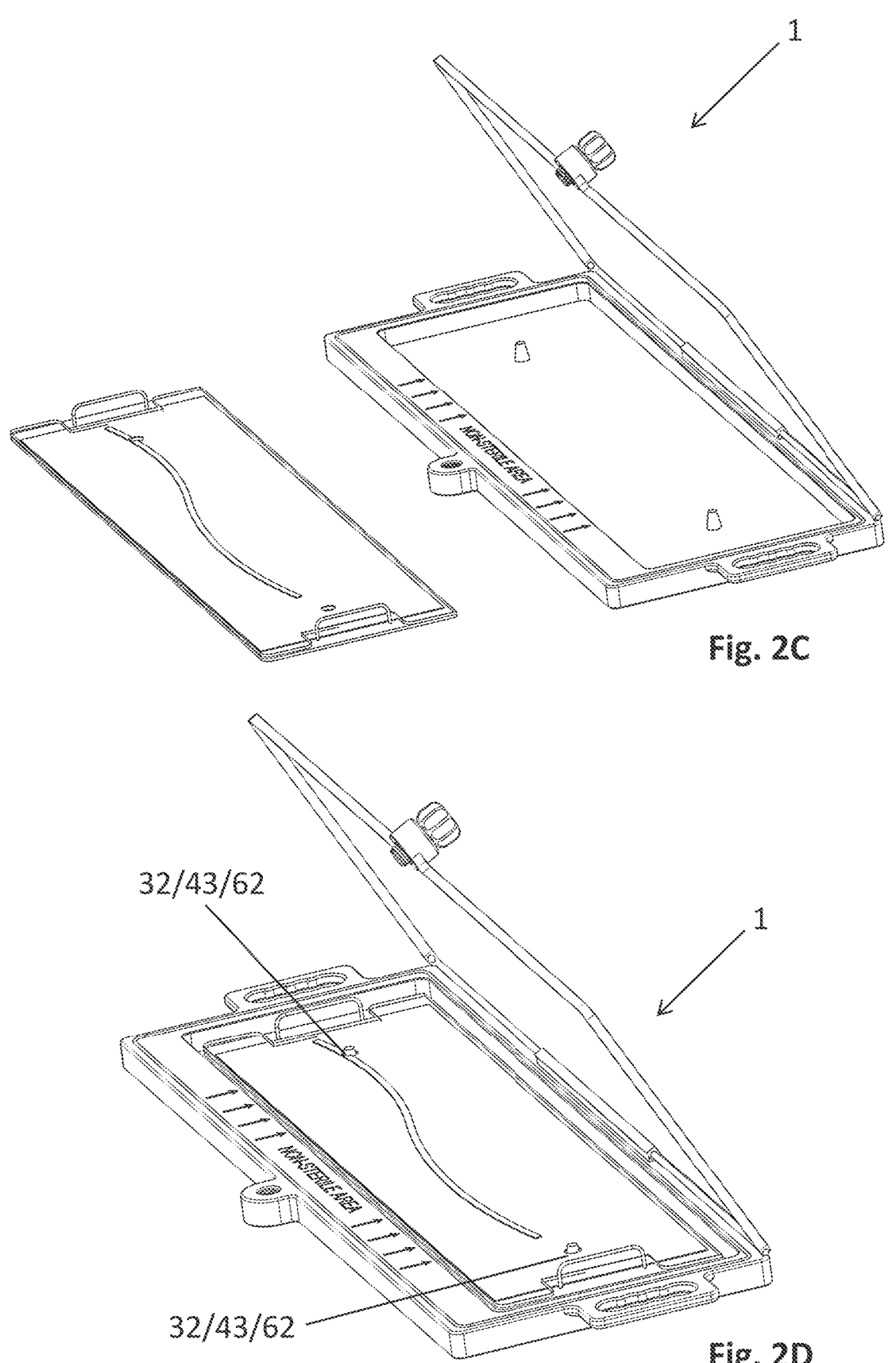
Figures 2E, 2F, 2G:
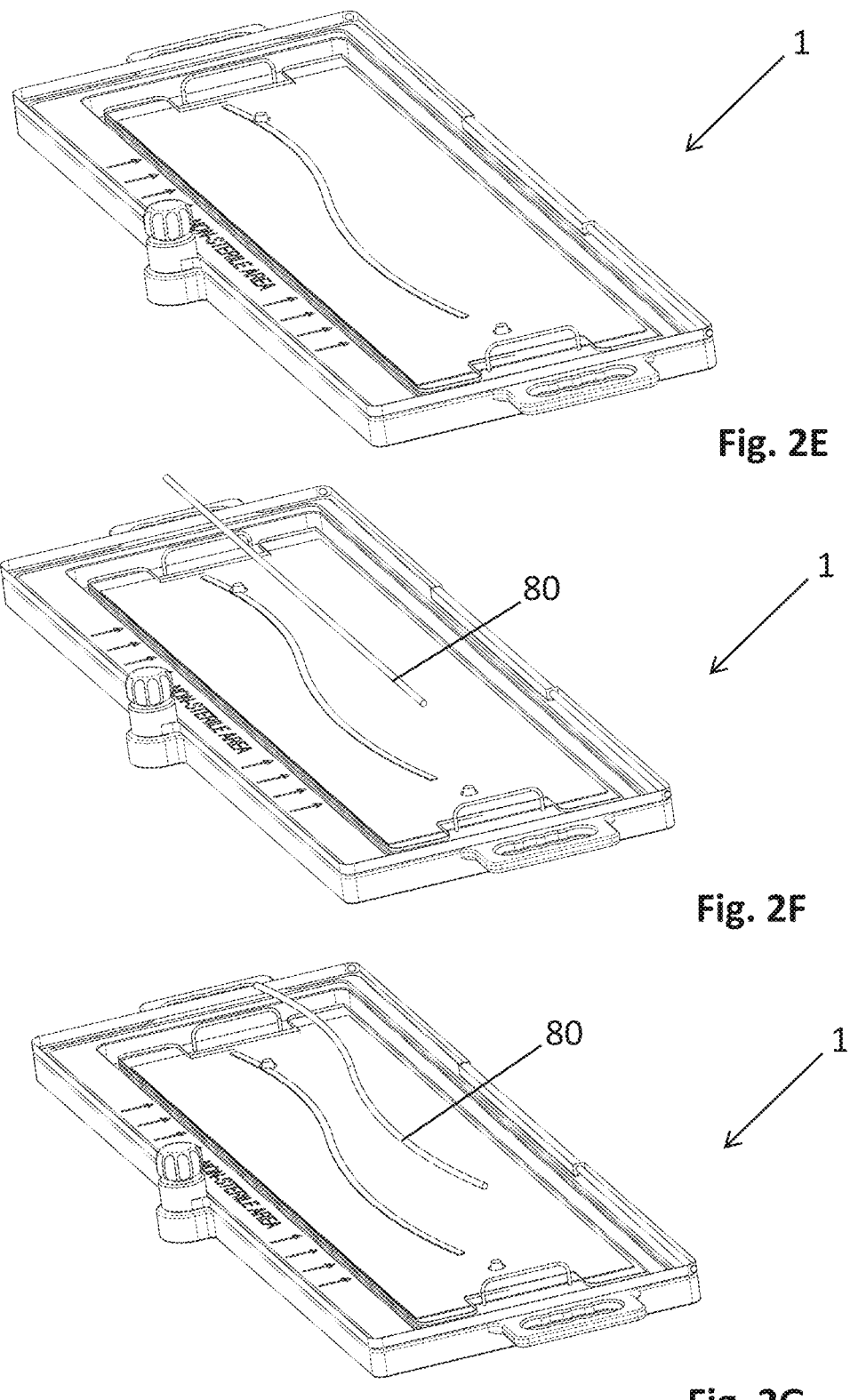
FIGS. 2E to 2G depict the rod shape visualisation device of FIGS. 2A to 2D in a closed state, according to the further embodiment of the present invention.

FIGS. 2A to 2G show an example rod shape visualisation device 1 in different perspective views, namely in a first, open state (FIGS. 2A to 2D) and in a second, closed state (FIGS. 2E to 2G). In this example, the rod visualisation template 40 is made of a sheet of paper or similar. The advantage of using one or more attached sheets of paper is that the template can be produced or printed with common office infrastructure. The disadvantage of a sheet of paper or similar is its higher flexibility. This flexibility or missing stiffness imposes a risk when transferring the non-sterile visualisation template 40 into the sterile case 10. There is a higher risk that the visualisation template comes in contact with the sterile area.

To overcome this risk, as shown in FIGS. 2A to 2G, the visualisation template is captured in a stable shell, casing, holding means or covering 60. The casing may be formed as an inner box 90, optionally with an inner box cover 91. This covering provides sufficient rigidity for a safe transfer. To provide visibility of the visualisation template, at least one side is transparent. In this example, the covering 60 comprises at least one grip, handhold or handle 61 to facilitate a safe placement.

In this example, the covering 60 and/or the visualisation template 40 further comprise(s) at least one first placement reference 43, 62, which matches a complementarily arranged second placement reference 32 of the sterile case 10.

FIGS. 2A to 2G further show the method for operating the rod shape visualisation device 1.

FIGS. 2A and 2B show the visualisation template being placed into the shell.

FIG. 2C shows the shell including the visualisation template being placed into the sterile case.

FIG. 2D shows the shell including the visualisation template in situ in the sterile case.

FIG. 2E shows the sterile case in the closed state.

FIG. 2F shows a straight, unbent rod 80, which is held adjacent to the visualisation template.

FIG. 2G shows how the rod 80 has been contoured and sized according to the desired size and shape as depicted on the visualisation template.

FIGS. 3A to 3E show another embodiment of the present invention. In this example, the rod shape visualisation device 1 comprises a rod holder 70 to hold the spinal rod. FIGS. 3A to 3E show an implementation, according to which the rod holder is a fixed or integral part of the cover 13. Alternatively, the rod holder may be a modular part, or may be an integral part of the housing portion 11. The rod holder 70 comprises a rod clamping means or element 71. In this example, the clamping means is a screw clamp. Alternatively, a clamping means may be configured as a knee-toggle clamp, cam action clamp, etc.

Furthermore, the covering 60 and/or the visualisation template comprise(s) at least one first placement reference 43, 62 which matches a complementarily arranged second placement reference 32 of the sterile case 10. These placement references ensure that the position of the graphical image or representation 42 matches the position of the rod holder 70 and the rod clamping means 71.

FIGS. 3A to 3E further show the method for operating the rod shape visualisation device 1.

Figures 3A, 3B:
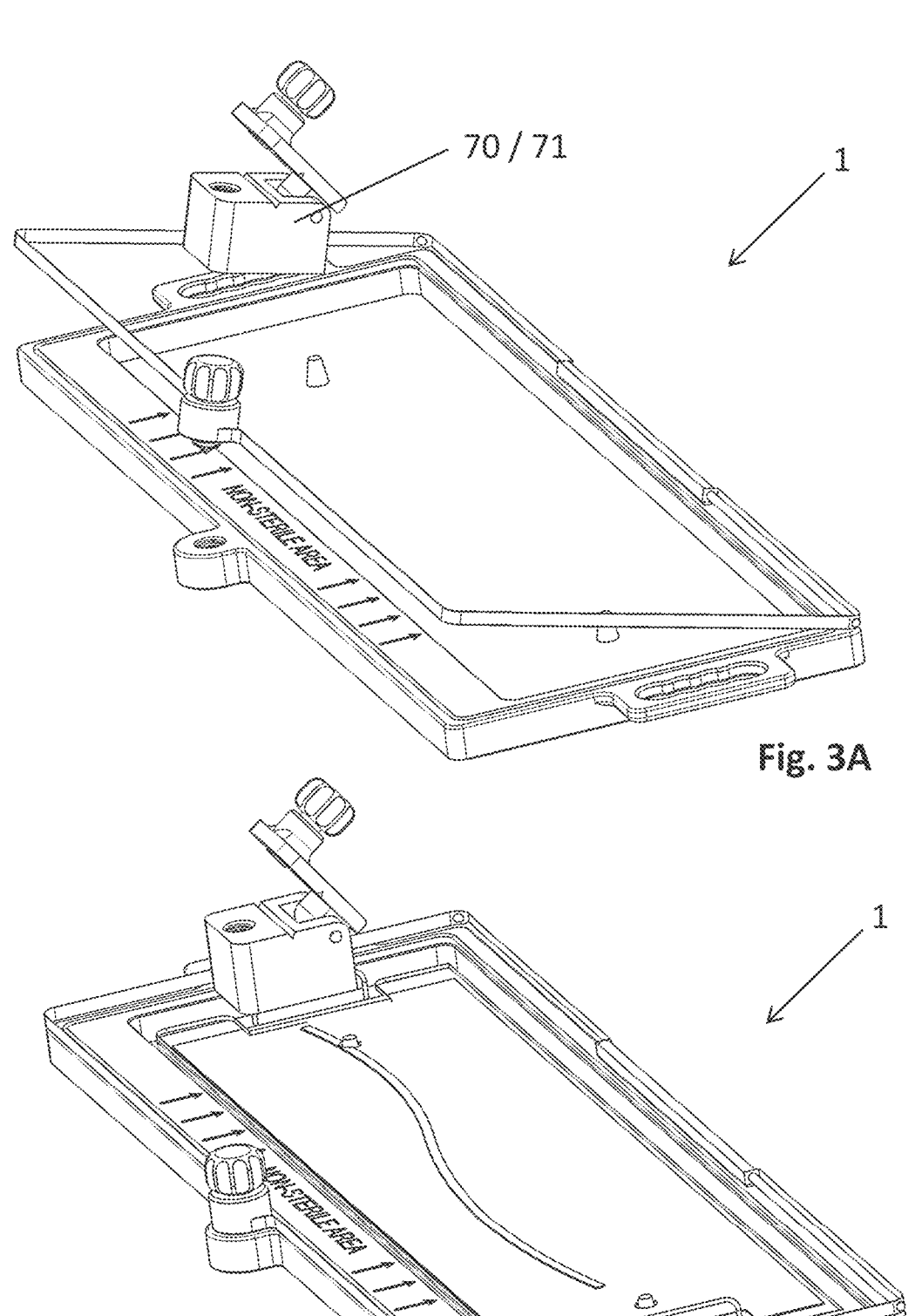
FIGS. 3A to 3E depict an example rod shape visualisation device in an open state and in a closed state, wherein the rod shape visualisation device comprises a rod holder.

FIG. 3A shows the rod shape visualisation device in the open state.

FIG. 3B shows the shell including the visualisation template placed in the sterile case. The rod holder is now open.

Figures 3C, 3D, 3E:
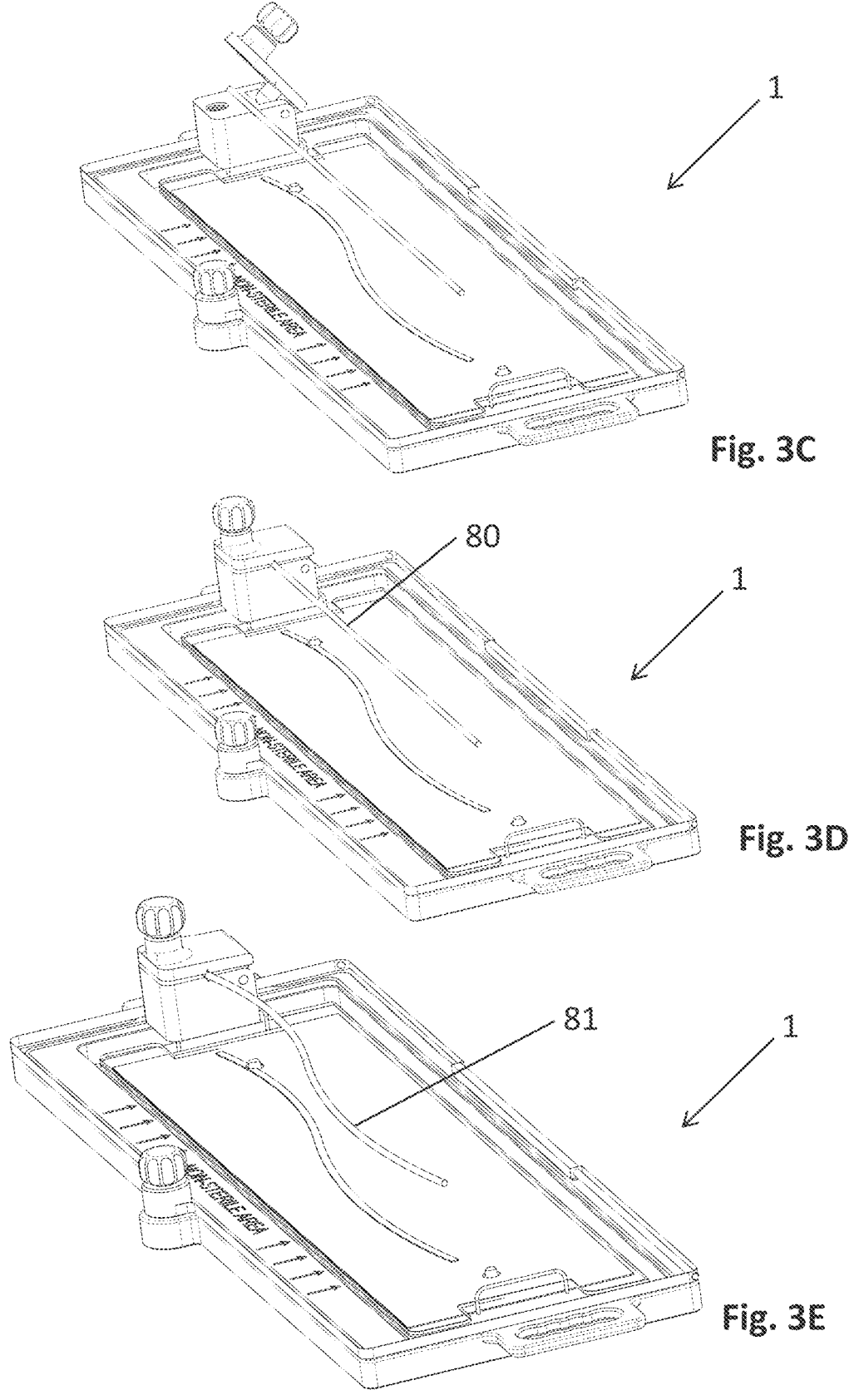
Figures 4A, 4B, 4C, 4D:
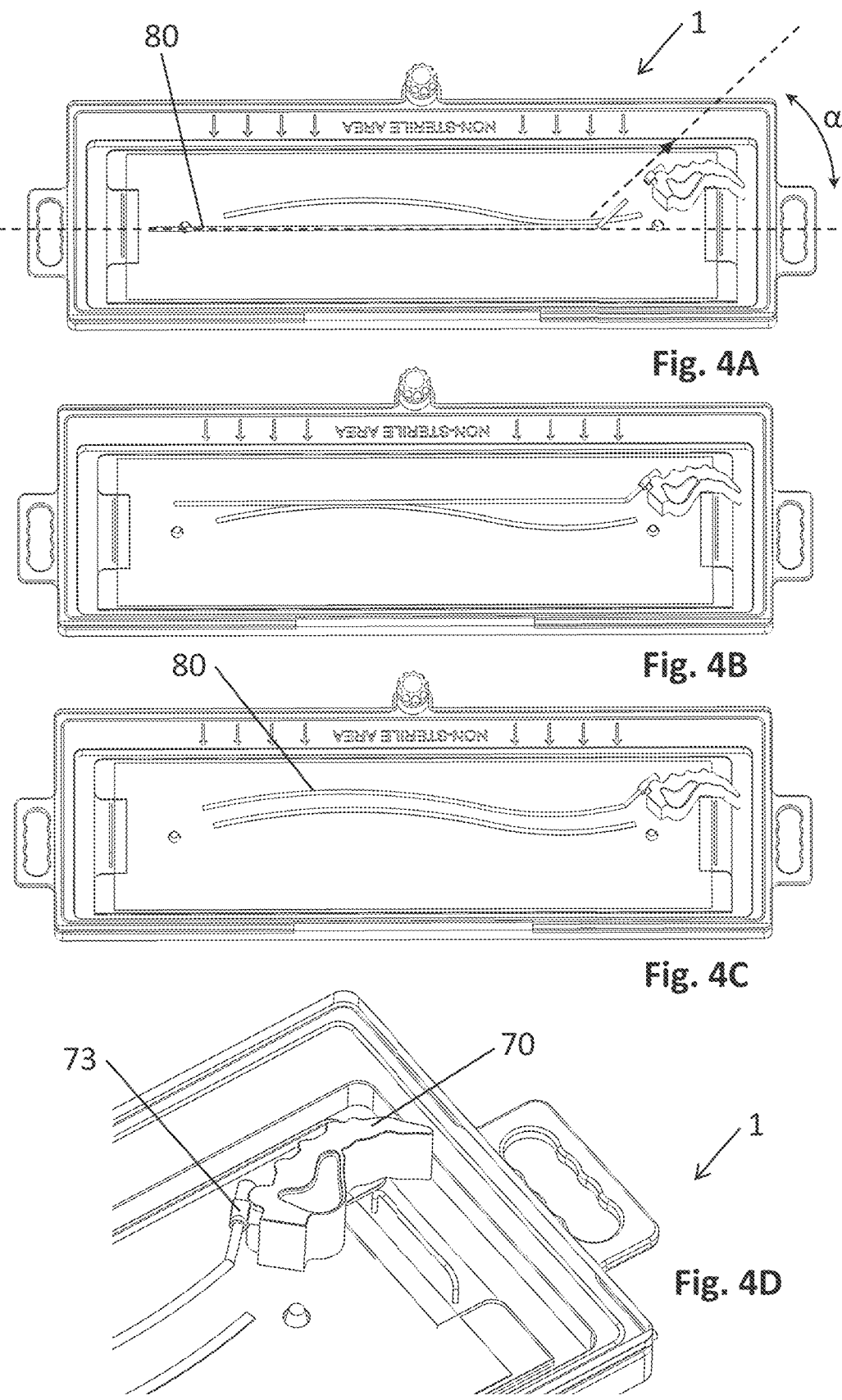
FIGS. 4A to 4D depict an example rod shape visualisation device in an open state and in a closed state, wherein the rod shape visualisation device comprises a rod holder which is shaped as a sacrum bone including a reference means which links or refers to a pre-operative reference point.

FIG. 3C shows how the rod 80 is placed or received in the rod holder.

FIG. 3D shows how the rod holder is clamping a straight, unbent rod 80, which is adjacent to the visualisation template. More specifically, in this example, the rod is placed above or substantially above the visualisation template (assuming the rod shape visualisation device lies on a horizontal surface).

FIG. 3E shows a situation, where the rod 80 has been contoured and sized according to the desired size and shape as depicted on the visualisation template.

FIGS. 4A to 4D show an alternative variant of the rod holder 70. The rod holder 70 is shaped as the sacral bone (in this case the human sacral bone) and so forms a clear spatial reference to the pre-operatively planned rod shape. Typically, a pre-operative planning is made based on an image of the full spine including sacral bone. The sacral bone is taken as a fixed landmark during the whole pre-operative planning procedure. In this example, the rod is held in a bore or channel. As depicted, the start point of the rod is mimicked by an abstract representation 73 of a sacral screw and a rod end. The sacral screw typically is a start point, base point in longer spinal fusion procedures and forms the start reference in surgical planning and the surgical procedure. Typically, given the anatomy of the human spine and the normal spatial ratio between spine and pelvis alignment, this rod end is oriented at an angle of 30° to 55°, more preferably 40° to 45° in relation to the length or longitudinal direction or axis of the sterile case.

Figures 5, 6:
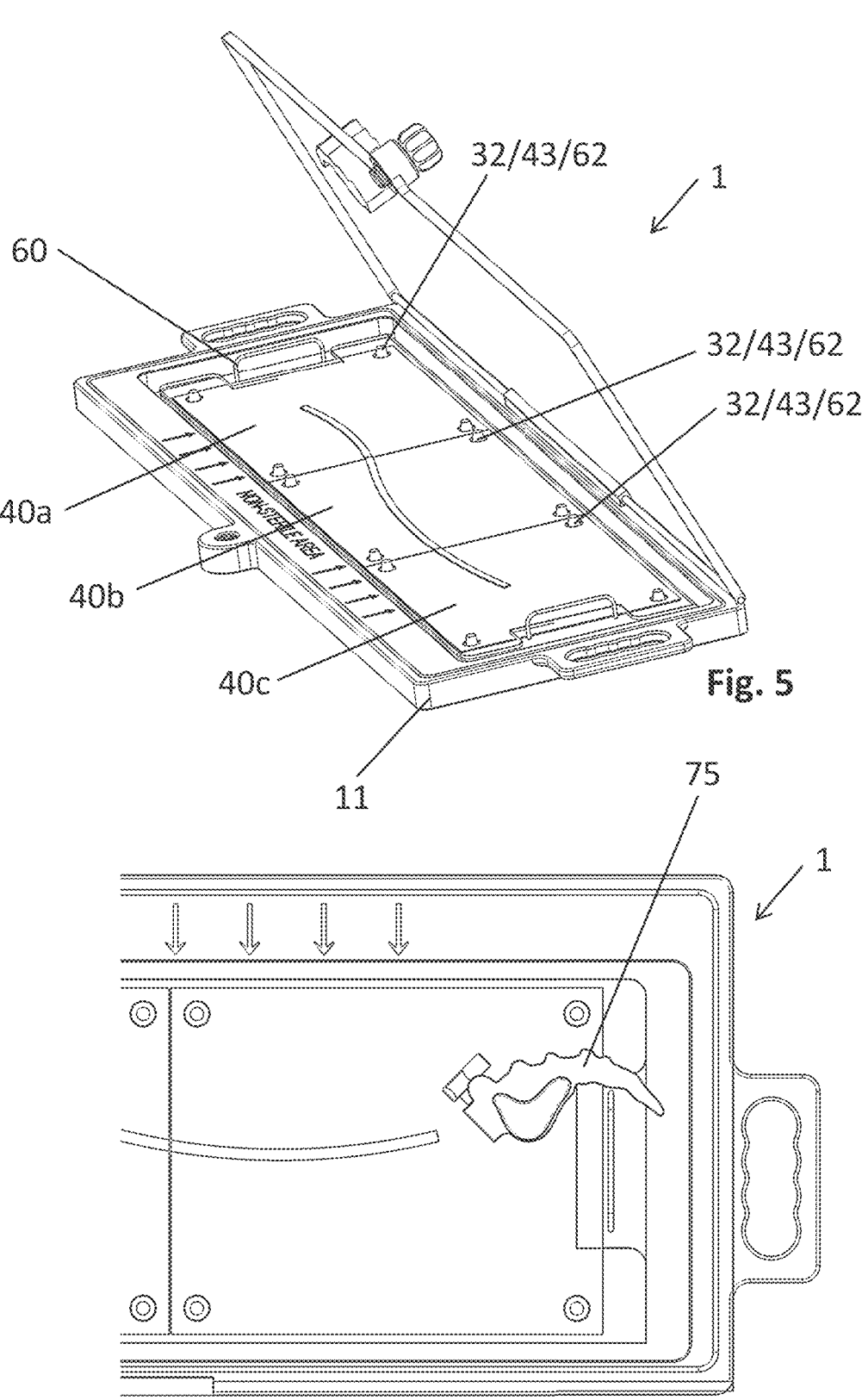
FIG. 5 depicts an example rod shape visualisation device in an open state, wherein the visualisation template is built out of multiple smaller visualisation templates.
FIG. 6 depicts an example rod shape visualisation device, wherein the cover comprises a start reference shaped as the image of the sacrum bone.

FIG. 5 illustrates another aspect of the invention. In this example, the visualisation template 40 is built of multiple smaller visualisation templates 40a, 40b, 40c. The advantage of using a plurality of smaller templates or sub-templates is that for example standard-sized paper or cardboard can be used and produced with more standard office equipment. For alignment, the covering 60 and/or visualisation templates 40a, 40b, 40c comprise at least one first placement reference 43, 62, which matches a complementarily arranged second placement reference 32 of the sterile case 10. These placement references ensure that the position of the graphical image or representation 42 matches the position of the rod holder 70. Advantageously, the respective sub-template and optionally the covering 60 comprises each at least two first placement references 43, 62 matching complementarily arranged second placement references 32 of the sterile case 10.

FIG. 6 shows an example rod shape visualisation device wherein a start reference 75, more specifically the sacral bone including a sacral screw and a rod portion, is etched, printed or otherwise indicated on the transparent surface and overlaps at least a portion of the visualisation template in this example.

FIGS. 7A to 7E depict an example rod shape visualisation device including a template holder in an open state and in a closed state, and comprising an adhesive tape sealing mechanism and an inner-box-shaped template holder.

In this example at least one of the visualisation device elements is manufactured by means of thermoforming. Thermoforming is a process of heating a thermoplastic sheet to its softening point. The sheet is stretched across a single-sided mould and then manipulated. Then, it cools into the desired shape. The most common methods to get the sheet to conform to its final shape are vacuum-forming, pressure-forming, and mechanical forming. The use of sheets of plastic which may be on a roll of raw material allows for a very cost-efficient production of single-use components. Food blister packaging is a typical example of a thermoformed component.

In accordance with the example as described in connection with FIGS. 1A to 1G and 2A to 2G, the example rod shape visualisation device 1 comprises a sterile case 10 serving as a sterility barrier, and a visualisation template 40 serving as an information providing means or element which is intended to be captured in a stable shell, casing, holding means or covering 60.

The sterile case 10 comprises a housing (portion) or main body portion 11 with an entrance aperture or opening 12 and a closure lid or cover 13, which is sized and shaped to close the entrance aperture 12. In this example, the housing portion is a box-shaped housing portion having an inner lumen, cavity or space 14. The boxed-shaped housing portion 11 has a bottom wall and a first sidewall 15a, a second sidewall 15b, a third sidewall 15c, and a fourth sidewall 15d. Each sidewall respectively has an inside surface or wall 17a, 17b, 17c, 17d, a topside 18a, 18b, 18c, 18d, and an outside surface or wall 19a, 19b, 19c, 19d. The first, second, third, and fourth topsides, respectively, have a first, second, third, and fourth thickness 'T1', 'T2', 'T3', 'T4'.

The inner lumen has an average first depth 'D1', an average first width 'W1' and an average first length 'L1'.

Further, in this example, the cover 13 is connected to the housing at one sidewall by a hinge coupling 16 or a compliant flexure mechanism allowing rotation of the cover in relation to the box-shaped housing portion.

To rigidly close the cover 13, and to provide the required sealing characteristics, the sterile box in this example comprises at least one releasable or non-releasable locking mechanism 20 configured as an adhesive tape 92 on the inner side 95 of the cover in such a manner that it will come in contact with one of the topside(s) of the housing portion 11. The adhesive tape in this example comprises a protective cover 93 inhibiting adhesive contact before executing the final closing procedure. Alternatively, the adhesive tape may be arranged at least on one of the topsides 18a, 18b, 18c, 18d in such a manner that it will come in contact with the inner side of the cover.

In this example, the housing is made of a foil-basis material processed by thermoforming. The sidewalls are obliquely directed inwardly towards the bottom wall to facilitate the manufacturing and to allow easy release of the mould-tooling. Advantageously, this converging shape of the inner lumen also provides a self-centring mechanism to place the visualisation template and/or covering.

In this example, the casing 60 is formed as an inner box 90, optionally with an inner box cover 91. This cover provides sufficient rigidity for a safe transfer. To provide visibility of the visualisation template, at least one side is transparent. The case 60 may comprise at least one grip, handhold or handle portion to facilitate its safe placement.

FIGS. 7A to 7E further show the method for operating the rod shape visualisation device 1.

Figure 7A:
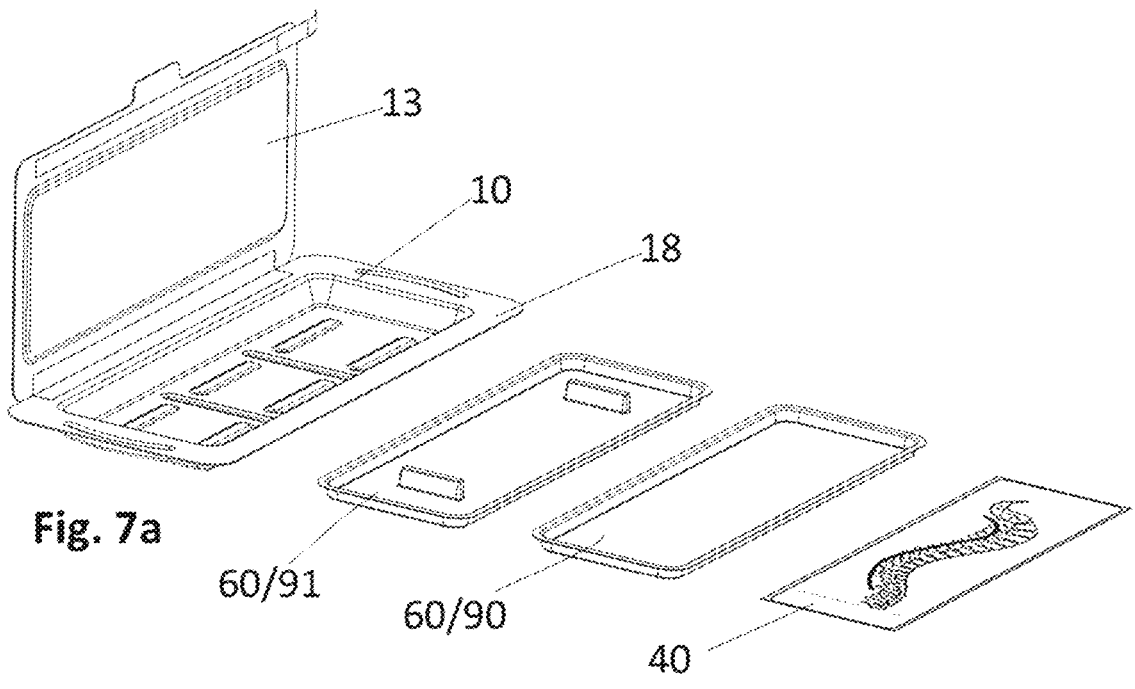
FIGS. 7A to 7E depict an example rod shape visualisation device in an open state and in a closed state with an adhesive tape sealing mechanism and an inner-box-shaped template holder.

FIG. 7A shows the individual components, namely the sterile case, the visualisation template 40, and the casing 60 consisting of the inner box 90 and the inner box cover 91.

Figure 7B:
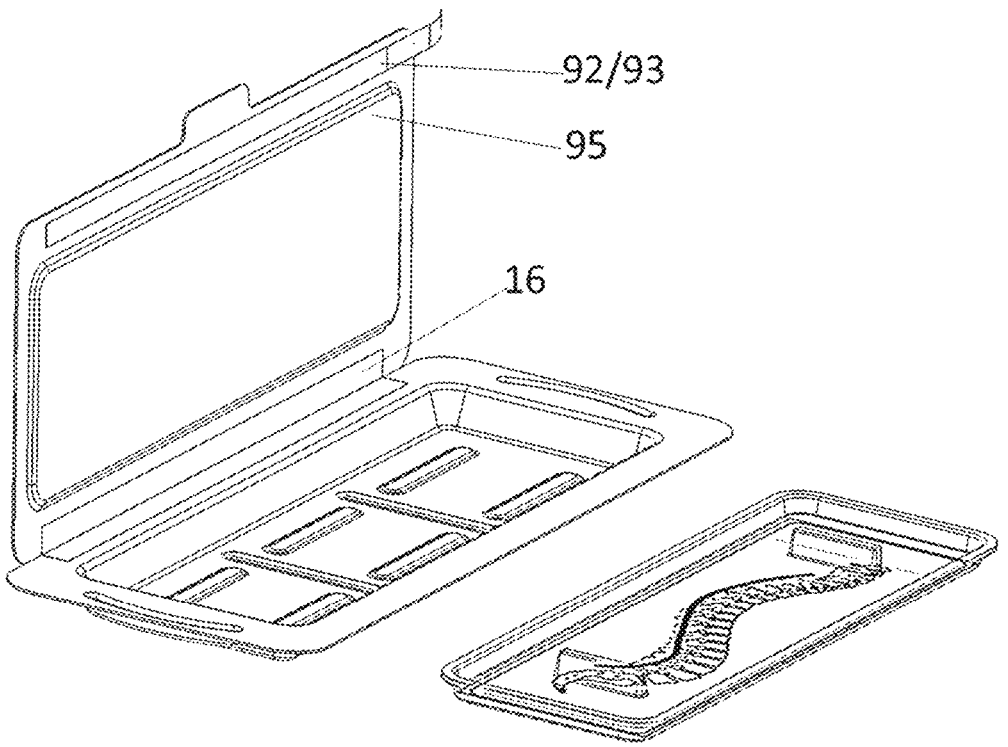

FIG. 7B shows the visualisation template being placed into the sterile case 10.

Figures 7C, 7D, 7E:
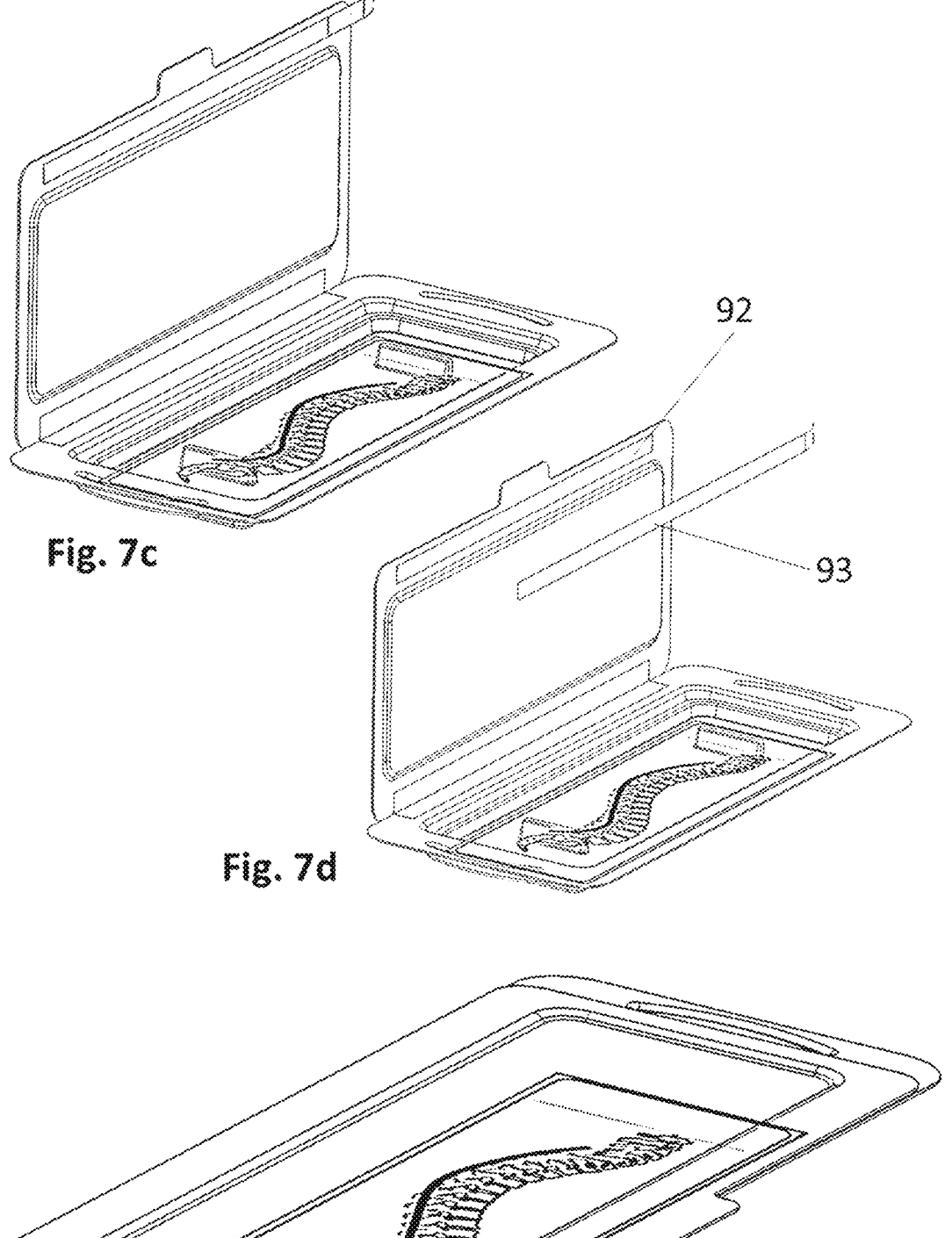

FIG. 7C shows the casing in situ in the sterile case.

FIG. 7D shows the step of removing the tape protective cover 93.

FIG. 7E shows the sterile case in the closed state. In the closed state, the displaying side 41 of the visualisation template 40 is arranged in the inner lumen 14 so that it is visible to the outside of the sterile case. The adhesive tape now seals the sterile case.

As described, the shape of the rod is typically based upon a pre-operative planning procedure. Based on X-rays, CT scans, MRI scans, or similar of the patient, the operating surgeon plans the desired shape of the rod using software. For this purpose, different software systems or brands exist. Typically, the software output of the planning result is an image of the patient's spine including a graphical representation of the rod. Most often, the size of this output does not represent the actual size in reality due to a scaling factor. As described for one example, the rod visualisation template is printed or reproduced on one or more sheets of paper, plastic foil, etc. Most efficiently, the sheet format is a standardised format (such as DIN A4, US Letter, etc.) and can be processed with standardised office equipment. To be able to translate the planning image to a correctly sized image on a visualisation template, a scaling method may be needed.

In a preferred embodiment, the scaling to real size is executed automatically by a rod shape visualisation device accompanying scaling software that recognises, converts and adapts any planning image to a real size image. Example adaptation variables to be considered are one or more of the following: correct scaling factor, length of image versus the division over the target number of sheets, printer and sheet border margins, orientation of the spine in relation to the sheet layout, connection or alignment references if for example the graphical representation of the rod is divided over multiple sheets, the size of the template holding means, etc.

The method of visualisation of a spinal rod size and shape in a sterile surgical area can be summarised with the steps of:

obtaining a surgical image of the spine;

planning a desired rod shape using the image of the spine;

optionally scaling the image to a real size image of the spine;

visualising the (scaled) image on the visualisation template 40 of the rod shape visualisation device 1;

placing the visualisation template into the housing portion 11 of the sterile case 10 of the rod shape visualisation device 1; and closing the cover 13 of the sterile case 10 to reach the closed state of the rod shape visualisation device 1.

In the close state, the visualisation template 40 is visibly arranged in the inner lumen 14 of the sterile case 10.

While the invention has been illustrated and described in detail in the drawings and foregoing description, such illustration and description are to be considered illustrative or exemplary and not restrictive, the invention being not limited to the disclosed designs. Other embodiments and variants are understood, and can be achieved by those skilled in the art when carrying out the claimed invention, based on a study of the drawings, the disclosure and the appended claims. New embodiments or variants may be obtained by combining any of the above teachings.

In the claims, the word "comprising" or "including" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A rod shape visualisation kit comprising a rod shape visualisation device for providing information on the desired shape of a posterior spinal rod during a bending process whilst being arranged in a sterile operation area, the rod shape visualisation device comprising:

a sterile case comprising a main body portion including an entrance aperture, and a cover, sized and shaped to seal the entrance aperture, the sterile case further comprising an inner cavity configured to come in contact with non-sterile or sterile objects, a non-sterile or sterile visualisation template comprising a displaying side providing information on the desired shape of a posterior rod, wherein the rod shape visualisation device defines a first, open state in which the cover is open, and a second, closed state in which the cover is closed, wherein in the closed state the displaying side of the visualisation template is visibly arranged in the inner cavity, and wherein the rod shape visualisation kit further comprises scaling software.

2. The rod shape visualisation kit according to claim 1, wherein the visualisation template is a thin single-use object including a graphical image or representation of the desired rod size and shape.

3. The rod shape visualisation kit according to claim 1, wherein the visualisation template is made of a medium or material selected from paper, cardboard, foil, plastic, steel, aluminium or any combination thereof.

4. The rod shape visualisation kit according to claim 1, wherein the visualisation template is a screen of an electronic device, which is configured to display the desired rod size and shape.

5. The rod shape visualisation kit according to claim 1, wherein the main body portion comprises sidewalls comprising topsides, the sidewalls defining a periphery of the inner cavity, wherein at least one of the sidewalls and/or the periphery comprises at least one marking or different colour indicating a border of an area in which contact with non-sterile objects or persons is allowed.

6. The rod shape visualisation kit according to claim 1, wherein at least one side of the main body portion and/or the cover is transparent.

7. The rod shape visualisation kit according to claim 1, wherein at least one side of the main body portion and/or the cover is electrically conductive to operate as a touchscreen.

8. The rod shape visualisation kit according to claim 1, wherein the cover is coupled to the main body portion by a hinge coupling.

9. The rod shape visualisation kit according to claim 1, wherein the main body portion is a housing shaped as a box.

10. The rod shape visualisation kit according to claim 1, wherein the main body portion and/or the cover has/have at least one handle.

11. The rod shape visualisation kit according to claim 1, wherein the visualisation template is captured in a stable shell or covering.

12. The rod shape visualisation kit according to claim 11, wherein the shell or covering comprises at least one handhold.

13. The rod shape visualisation kit according to claim 1, wherein the cover and/or visualisation template comprises at least one first placement reference which matches a complementarily arranged second placement reference of the sterile case.

14. The rod shape visualisation kit according to claim 1, wherein the rod shape visualisation device comprises a rod holder to hold the spinal rod.

15. The rod shape visualisation kit according to claim 1, wherein the rod shape visualisation device comprises a rod holder to hold the spinal rod, and wherein the rod holder is shaped as a sacral bone.

16. The rod shape visualisation kit according to claim 1, wherein the visualisation template is built of a plurality of smaller visualisation sub-templates.

17. The rod shape visualisation kit according to claim 16, wherein the sub-templates are of a standardised sheet format.

18. The rod shape visualisation kit according to claim 1, wherein the scaling software is configured to divide the length of an image over the target number of sheets.

19. The rod shape visualisation kit according to claim 1, wherein the sterile case is a box, container, envelope, bag, or pouch.

20. A rod shape visualisation device for providing information on the desired shape of a posterior spinal rod during a bending process whilst being arranged in a sterile operation area, the rod shape visualisation device comprising:

a sterile case comprising a main body portion including an entrance aperture, and a cover, sized and shaped to seal the entrance aperture, the sterile case further comprising an inner cavity configured to come in contact with non-sterile or sterile objects, a non-sterile or sterile visualisation template comprising a displaying side providing information on the desired shape of a posterior rod, wherein the rod shape visualisation device defines a first, open state in which the cover is open, and a second, closed state in which the cover is closed, wherein in the closed state the displaying side of the visualisation template is visibly arranged in the inner cavity, and wherein the visualisation template is a screen of an electronic device, which is configured to display the desired rod size and shape.

21. The rod shape visualisation device according to claim 20, wherein the main body portion comprises sidewalls comprising topsides, the sidewalls defining a periphery of the inner cavity, wherein at least one of the sidewalls and/or the periphery comprises at least one marking or different colour indicating a border of an area in which contact with non-sterile objects or persons is allowed.

22. The rod shape visualisation device according to claim 20, wherein at least one side of the main body portion and/or the cover is transparent.

23. The rod shape visualisation device according to claim 20, wherein at least one side of the main body portion and/or the cover is electrically conductive to operate as a touchscreen.

24. The rod shape visualisation device according to claim 20, wherein the cover is coupled to the main body portion by a hinge coupling.

25. The rod shape visualisation device according to claim 20, wherein the rod shape visualisation device comprises a rod holder to hold the spinal rod.

26. The rod shape visualisation device according to claim 20, wherein the sterile case is a box, container, envelope, bag, or pouch.

\* \* \* \* \*